United States Patent [19]

Bouvet et al.

[11] Patent Number: 4,509,509
[45] Date of Patent: Apr. 9, 1985

[54] APPARATUS FOR TREATING THE JOINTS OF THE HUMAN BODY

[76] Inventors: Jean Bouvet, 1319 Butterfield Rd., San Anselmo, Calif. 94960; Robert D. Teasdale, 307A Third St., Sausalito, Calif. 94965

[21] Appl. No.: 512,669

[22] Filed: Jul. 11, 1983

[51] Int. Cl.³ .............................................. A61H 29/00
[52] U.S. Cl. .................................. 128/24.1; 128/25 R; 128/363
[58] Field of Search ............................... 128/419–423, 128/24.1, 25 R, 25 B, 80 D, 80 G, 733, 795–796, 71, 75, 44, 51, 68.1, 363

[56] References Cited

U.S. PATENT DOCUMENTS

| 1,498,529 | 6/1924 | Allen | 128/796 X |
| 2,696,206 | 12/1954 | Bierman | 128/25 B |
| 4,235,437 | 11/1980 | Ruis et al. | 272/134 |
| 4,323,060 | 4/1982 | Pecheux | 128/75 X |
| 4,421,336 | 12/1983 | Petrofsky et al. | 128/421 X |

FOREIGN PATENT DOCUMENTS

| 2213757 | 9/1973 | Fed. Rep. of Germany ... 128/423 R |
| 644469 | 1/1979 | U.S.S.R. ............................... 128/25 R |

Primary Examiner—Robert A. Hafer
Assistant Examiner—Chris Coppens
Attorney, Agent, or Firm—Melvin R. Stidham

[57] ABSTRACT

Apparatus for treating human joints wherein a machine reciprocates to flex the joint while an electrical stimulator causes contraction of muscles affected by the flexing. Switches disposed along the path of machine movement are tripped to energize the stimulator current during selected stages of the machine movement, and in either or both directions.

6 Claims, 2 Drawing Figures

APPARATUS FOR TREATING THE JOINTS OF THE HUMAN BODY

BACKGROUND OF THE INVENTION

Currently there are several different modalities of passive therapy for treatment of human joints. According to one method, one or more electrical stimulator is strapped or otherwise applied to the skin of the patient and electrical impulses are applied at appropriate intensities and frequencies to cause muscle contraction. In accordance with another system, a limb is strapped or otherwise supported on a machine that moves back and forth to flex a joint of the limb, e.g. a knee, elbow or shoulder, while the patient is wholly passive.

OBJECTS OF THE INVENTION

It is an object of this invention to provide apparatus for treatment of the human joints that combines the advantages of both the electrical stimulator and the passive motion machine in a manner that may exceed their combined effects.

It is a further object of this invention to provide apparatus that energizes an electrical stimulator in predetermined coordination with a passive motion machine so that electrical stimulation of muscle contraction is induced at selected, strategic stages in the passive flexing of a joint.

Other objects and advantages of this invention will become apparent from the description to follow, particularly when read in conjunction with the accompanying drawing.

SUMMARY OF THE INVENTION

In carrying out this invention we combine with a passive motion machine, an electrical stimulator to be applied to the muscles that are extended and contracted in the course of flexing. Switch means in the stimulator circuit are activated at selected stages to the cycle of the passive motion machine so that the electrical stimulator is energized during adjusted, predetermined stages of the flexing cycle, whereby the two forms of treatment are closely coordinated.

DESCRIPTION OF A PREFERRED EMBODIMENT

Figure 1:
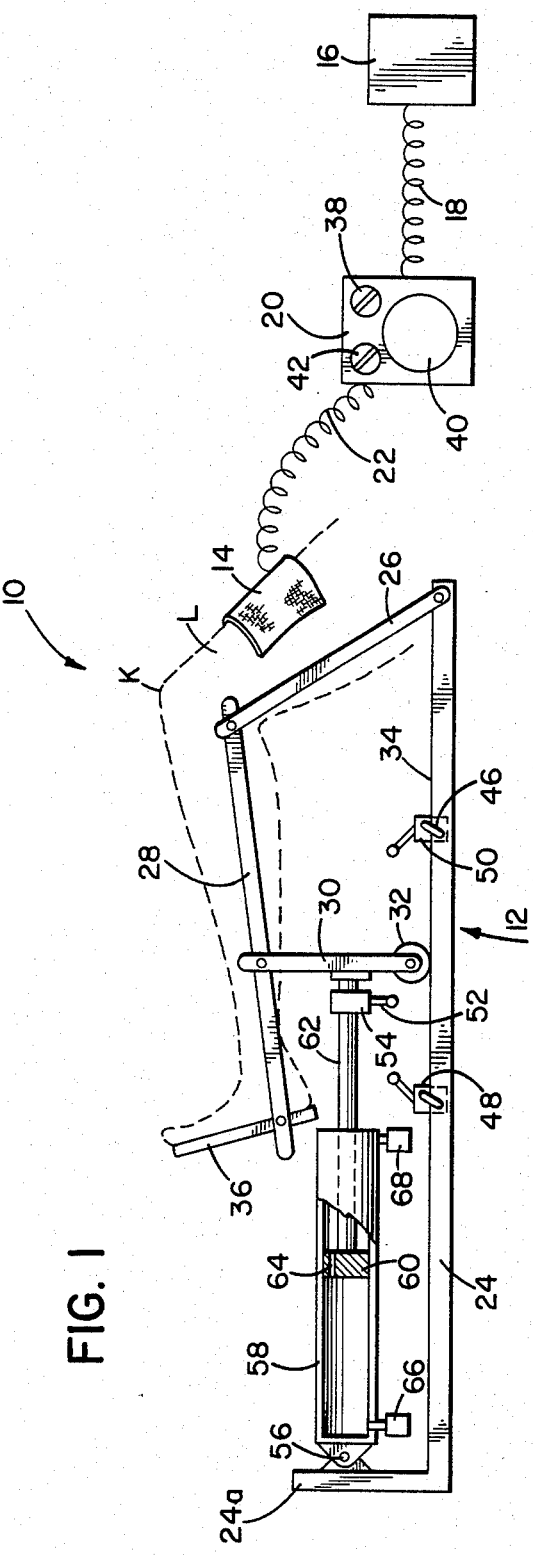
FIG. 1 is a side elevation, partially broken away, of joint treating apparatus embodying features of this invention.

Referring now to FIG. 1 with greater particularity, the joint treating apparatus 10 of this invention includes a passive motion machine 12 and one or more electrical stimulator pad 14 to be taped or otherwise secured to the patient's limb L over a selected muscle, which actuates the joint K being treated. Electric current from the stimulator control box 16 is delivered through cable 18 to a control panel 20 and through cable 22 to the stimulator pad 14.

The passive motion machine 12 includes a base 24, at one end of which is pivotally mounted an arm 26, which is oscillated by a suitable motor drive means (not shown). Pivotally mounted to the end of the arm 26 is limb support arm 28 so that, together they comprise a joint flexing linkage. The linkage 26, 28 is supported on a leg 30 carrying a slide or roller 32 at its lower end to slide or roll along a track 34 on the base 24. For use in the treatment of the leg muscles a foot support 36 may be carried at the end of the arm 28.

In operation, it is apparent that, as the arm 26 oscillates the upper leg L is moved back and forth to flex the knee K repeatedly. Of course, it is understood that an analogous arrangement may be made to flex other joints of the body, including the knee, ankle, elbow and shoulder.

Operated in conjunction with the passive motion machine 12, is a solenoid 40 and a four-position selector switch 42 that enables an operator to select the mode of operation, as will hereinafter be described.

The solenoid 40 is included in a control electrical circuit 44 which when completed, energizes the solenoid 40 from a source of current 45a, 45b. When the solenoid 40 is energized, its contact (not shown) closes to allow electric current to flow from the stimulator control box 16 to the electrode pad or pads 14. The stimulator control box is operative to deliver a current at a selected frequency, wave form and amplitude, and energization of the solenoid 40 results in delivery of the current having the selected parameters.

Included in the control panel 20 is a manual selector switch 38 that enables the electric stimulator 14 to be used independently of the passive motion machine 12 (see also FIG. 2B).

Selectively mounted in any position along the rail 34, as by means of wing nuts 46 are limit switches 48 and 50. The limit switches 48 and 50 are, engageable by an arm 52 which is secured at 54 to the linkage support leg 30. The switches are of the toggle type to be moved and locked into either one of two selected positions, on or off, depending upon the direction of movement of the linkage support leg 30. The limit switches 48 and 50 are conditioned so that, when in the position shown in FIG. 1 disposed toward each other, both switches are closed to enable current to flow to the solenoid 40.

In the position shown in FIG. 1, the passive motion device is approximately midway through its stoke and, assuming movement toward the left, it has closed switch 50 and is moving toward previously closed switch 48. Hence, during this stage of the reciprocation, with the knee K being flexed, the switches 48 and 50 are conditioned to enable current flow to the solenoid 40, closing its contact and enabling the stimulator current, at intensities and frequencies selected at the control box 16, to flow to the stimulator electrodes 14. Then, when the switch 48 is reached and triggered, the circuit is again opened to remain open until the switch 48 is closed on the return stroke.

Pivoted at 56 to an upright member 24a on the machine frame 24 is an air cylinder 58 in which a piston 60 is reciprocated by attachment of the piston rod 62 to the linkage support leg 30 by any suitable means 54. A small orifice 64 through the piston 60 enables transfer of air from one side of the piston 60 to the other as the piston reciprocates. Pressure switches 66 and 68, which are also provided in the control circuit 44 (FIG. 2) are closed by increase in pressure to which they are exposed. Hence, as the linkage support leg 30 and piston 60 move to the left in FIG. 1 the pressure is applied to the switch 66 to close it while pressure is reduced at switch 68 causing it to open. When the piston returns toward the right in FIG. 1, pressure is applied to the pressure switch 68 so that it is closed, while pressure is reduced at switch 66 so that it opens.

Figure 2:
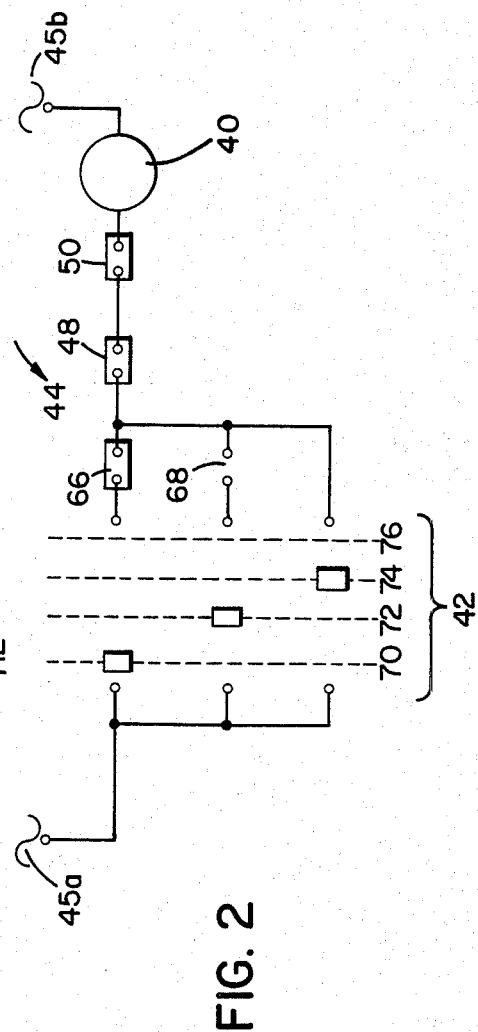
FIG. 2 is a wiring diagram forming a part of this invention.

Referring now to FIG. 2, the selector switch 42 may be turned in any one of four positions to select the mode of operation of the device 10 which will cause current to flow to the pad or pads 14. In position 70 current will flow through pressure switch 66, when it is closed, but not through pressure switch 68, so that the limit switches 48 and 50 are effective to energize the solenoid 40 and activate the stimulator only during movement to the left in FIG. 1, i.e. during leg extensions. In position 72 current will flow through pressure switch 68, when it is closed, but not through pressure switch 66, so that limit switches 48 and 50 are effective only during leg bending. In position 74, current will flow directly through limit switches 48 and 50, as the arm 54 moves between them to energize the solenoid 40 in both strokes of the linkage 26, 28; and in position 76 the circuit 44 is open throughout operation of the passive motion device 12 so that the electrical stimulator 14 is inactivated. Included in the control panel 20 is a manual switch 38 which may be closed to energize the stimulator 14 and bypass the solenoid 40.

While this invention has been described in conjunction with a preferred embodiment thereof, it is obvious that modifications and changes therein may be made by those skilled in the art to which it pertains without departing from the spirit and scope of this invention, as defined by the claims appended hereto.

What is claimed as invention is:

1. Apparatus for treating the joints of the human body comprising:
   a machine operative to support a human limb and, without physical participation of the patient, to flex a joint including same, while a portion on said machine moves back and forth along a given path; and
   an electrical stimulator including an electrode to be attached to the skin of the human body in areas over muscles affected by the flexing of a joint and a stimulator electric circuit with a signal source including said electrode;
   the improvement comprising:
   an electrically actuated switch device in said stimulator electric circuit;
   a control circuit with a source of control current;
   said electrically actuated switch device being in said control circuit to be energized thereby; and
   a pair of limit switches in said control circuit, each selectively positioned along said given path and engageable by said machine portion to energize said switch device during a predetermined stage of the back and forth movement thereof.

2. The apparatus defined by claim 1 including:
   a pair of direction switch devices in said control circuit, each conditioned to be closed in only one direction of movement of said machine portion.

3. The apparatus defined by claim 2 including:
   a selector switch in said control circuit operative when set in each of first and second positions to direct current in said control circuit through one of said direction control switch devices.

4. The apparatus defined by claim 3 wherein:
   said selector switch may be set in a third position to direct current around said direction control switch devices.

5. The apparatus defined by claim 3 wherein:
   said selector switch may be set in an inactive position to open said control circuit.

6. The apparatus defined by claim 1 including:
   a bypass conductor around said switch device and a manually operated switch in said bypass conductor.

* * * * *